United States Patent
Patraka (10) Patent No.: US 10,786,641 B1
(45) Date of Patent: Sep. 29, 2020

(54) MEDICAL TUBE SECURING DEVICE

(71) Applicant: Georgi Patraka, Cape Coral, FL (US)

(72) Inventor: Georgi Patraka, Cape Coral, FL (US)

( * ) Notice: Subject to any disclaimer, the term of this patent is extended or adjusted under 35 U.S.C. 154(b) by 425 days.

(21) Appl. No.: 15/689,116

(22) Filed: Aug. 29, 2017

(51) Int. Cl.
*A61M 16/04* (2006.01)
*A61M 25/02* (2006.01)

(52) U.S. Cl.
CPC ........ *A61M 16/0497* (2013.01); *A61M 25/02* (2013.01)

(58) Field of Classification Search
CPC ............ A61M 16/048; A61M 16/0497; A61M 16/0493; A61M 16/049; A61M 16/0495; A61M 2025/024; A61M 2025/0253; A61M 2025/026; A61M 25/02; A61M 25/022
USPC ....................................................... 128/200.26
See application file for complete search history.

(56) References Cited

U.S. PATENT DOCUMENTS

| | | | |
|---|---|---|---|
| D261,680 S | 11/1981 | Hall | |
| 4,307,903 A | 12/1981 | Wallace | |
| 4,516,293 A * | 5/1985 | Beran | A61M 25/02 128/207.17 |
| 4,683,882 A * | 8/1987 | Laird | A61M 16/0488 128/207.17 |
| 4,707,906 A * | 11/1987 | Posey | A61G 7/0503 128/DIG. 26 |
| 4,955,864 A * | 9/1990 | Hajduch | A61B 17/132 128/DIG. 15 |
| 5,282,463 A | 2/1994 | Hammersley | |
| 5,546,938 A | 8/1996 | McKenzie | |
| 5,782,236 A | 7/1998 | Ess | |
| 5,806,516 A * | 9/1998 | Beattie | A61M 16/0488 128/207.14 |
| 5,894,840 A * | 4/1999 | King | A61M 16/0488 128/200.26 |
| 6,293,945 B1 * | 9/2001 | Parins | A61B 18/1402 606/45 |
| 6,612,309 B1 | 9/2003 | Ancona | |
| 6,755,191 B2 * | 6/2004 | Bertoch | A61M 16/0488 128/200.26 |
| 7,131,168 B2 * | 11/2006 | Pangallo | B65D 63/1063 24/16 PB |
| 8,096,300 B2 | 1/2012 | Russo | |

(Continued)

FOREIGN PATENT DOCUMENTS

WO 2006060821 A1 6/2006

*Primary Examiner* — Samchuan C Yao
*Assistant Examiner* — Nathan M Le (57) ABSTRACT

The medical tube securing device is a fastener that is further adapted for use with a first and second catheter. The medical tube securing device fastens the first catheter to the second catheter. The medical tube securing device comprises an intubation strap, a gastric clip, and a latch. The intubation strap and the gastric clip are attached to the latch. The intubation strap and the latch attach the first catheter to the medical tube securing device. The gastric clip attaches the second catheter to the medical tube securing device thereby securing the first catheter to the second catheter. The first catheter is an endotracheal device and the second catheter is a gastric catheter. The medical tube securing device further comprises a bite guard that prevents the patient from biting one or more devices selected from the group consisting of the endotracheal device or the gastric catheter.

13 Claims, 4 Drawing Sheets

(56) References Cited

U.S. PATENT DOCUMENTS

| | | | | |
|---|---|---|---|---|
| 8,931,743 B2* | 1/2015 | Stango, Jr. | ............... | H02G 3/32 |
| | | | | 248/74.1 |
| 9,387,303 B2* | 7/2016 | Pittaway | ............. | A61M 5/1418 |
| 9,713,691 B2* | 7/2017 | Kirn | .................. | A61M 16/0488 |
| 2003/0226243 A1* | 12/2003 | Pangallo | ............... | F16L 3/2336 |
| | | | | 24/16 PB |
| 2004/0188571 A1* | 9/2004 | Stigler | ..................... | F16B 2/08 |
| | | | | 248/74.1 |
| 2009/0125002 A1* | 5/2009 | Totz | ..................... | A61M 16/04 |
| | | | | 604/528 |
| 2010/0078029 A1* | 4/2010 | McDonald | ........ | A61M 16/0488 |
| | | | | 128/207.14 |
| 2010/0294271 A1* | 11/2010 | Pittaway | ............. | A61M 5/1418 |
| | | | | 128/202.13 |
| 2013/0220328 A1* | 8/2013 | Jablonski | .......... | A61M 16/0875 |
| | | | | 128/205.25 |
| 2014/0261441 A1* | 9/2014 | Phillips | ............. | A61M 16/0497 |
| | | | | 128/207.14 |
| 2014/0261463 A1* | 9/2014 | Visconti | ............ | A61M 16/0493 |
| | | | | 128/861 |

\* cited by examiner

MEDICAL TUBE SECURING DEVICE

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of medical and veterinary science including devices for introducing media into a body, more specifically, a device for emplacing and holding a catheter.

The intubation of a breathing tube is a complicated process that requires: 1) the insertion of an endotracheal device into the tracheal tube; 2) the placement of the endotracheal device within tracheal tube; and, 3) the confirmation of the proper placement of the endotracheal device by taking x-rays of the patient. In the majority of cases, a need to intubate a person with an endotracheal device further requires the intubation of a gastric catheter into the esophagus. The interaction of the gastric catheter with the endotracheal device can dislodge the endotracheal device requiring the repositioning and additional x-rays to reconfirm the positioning of the endotracheal device within the patient.

The current best practice to avoid this situation is to use an adhesive tape to secure the gastric catheter to the endotracheal device. Because it is in the nature of adhesive tape to fail over time, particularly in medical environments, for patients who require an endotracheal device over a long period, the use of adhesive tape can only be considered a temporary solution.

Clearly a more permanent method to bind a gastric catheter to an endotracheal device would be of benefit.

SUMMARY OF INVENTION

This disclosure addresses the above issue.

The medical tube securing device is a fastener. The medical tube securing device is adapted for use with a first catheter. The medical tube securing device is further adapted for use with a second catheter. The medical tube securing device fastens the first catheter to the second catheter. The medical tube securing device comprises an intubation strap, a gastric clip, and a latch. The intubation strap and the gastric clip are attached to the latch. The intubation strap and the latch attach the first catheter to the medical tube securing device. The gastric clip attaches the second catheter to the medical tube securing device thereby securing the first catheter to the second catheter. In the first potential embodiment of the disclosure, the first catheter is an endotracheal device and the second catheter is a gastric catheter. In a subsequent potential embodiment of the disclosure, the medical tube securing device further comprises a bite guard that prevents the patient from biting one or more devices selected from the group consisting of the endotracheal device or the gastric catheter.

These together with additional objects, features and advantages of the medical tube securing device will be readily apparent to those of ordinary skill in the art upon reading the following detailed description of the presently preferred, but nonetheless illustrative, embodiments when taken in conjunction with the accompanying drawings.

In this respect, before explaining the current embodiments of the medical tube securing device in detail, it is to be understood that the medical tube securing device is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the medical tube securing device.

It is therefore important that the claims be regarded as including such equivalent construction insofar as they do not depart from the spirit and scope of the medical tube securing device. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Figure 1:
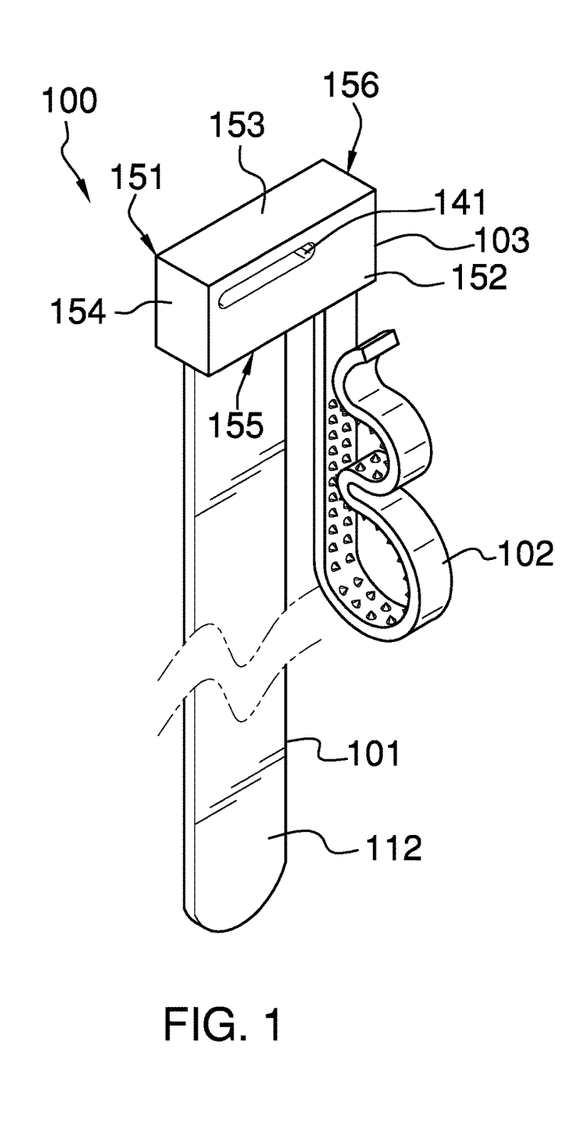
FIG. 1 is a perspective view of an embodiment of the disclosure.
Figure 2:
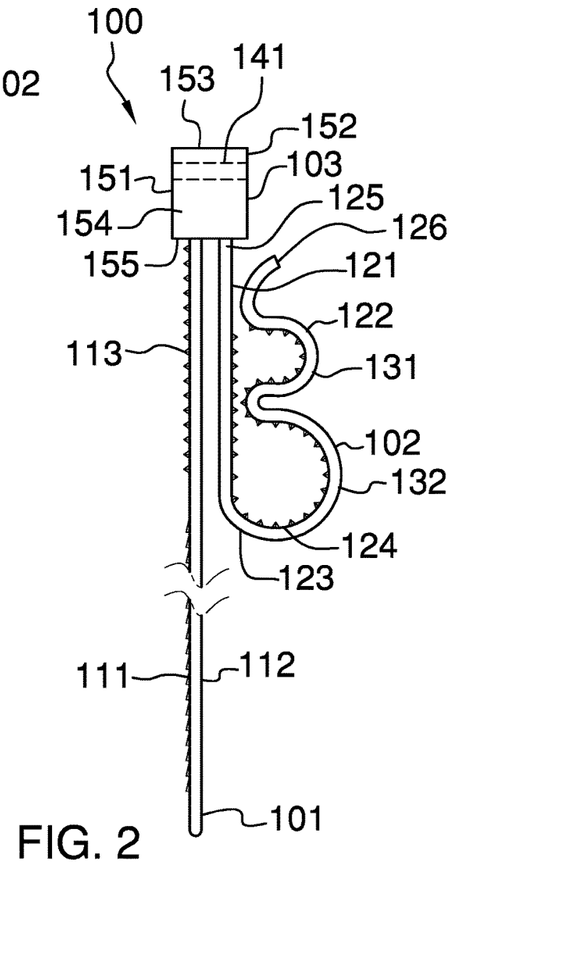
FIG. 2 is a side view of an embodiment of the disclosure.
Figure 3:
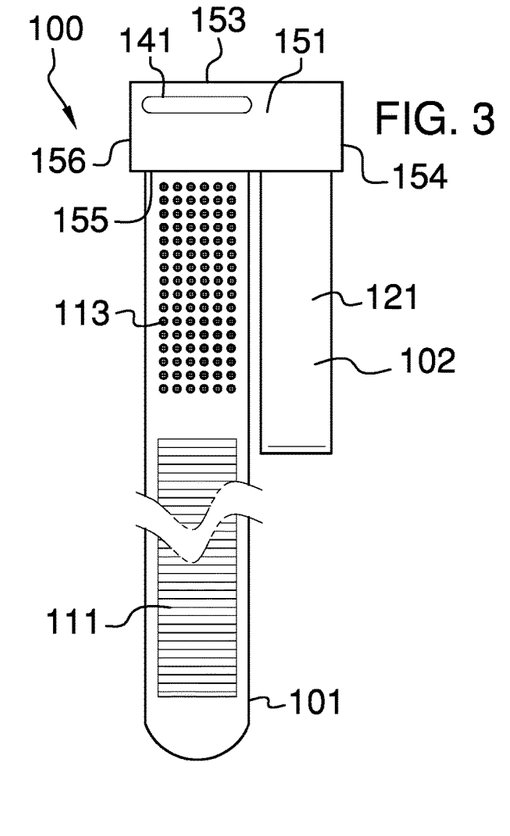
FIG. 3 is a rear view of an embodiment of the disclosure.
Figure 4:
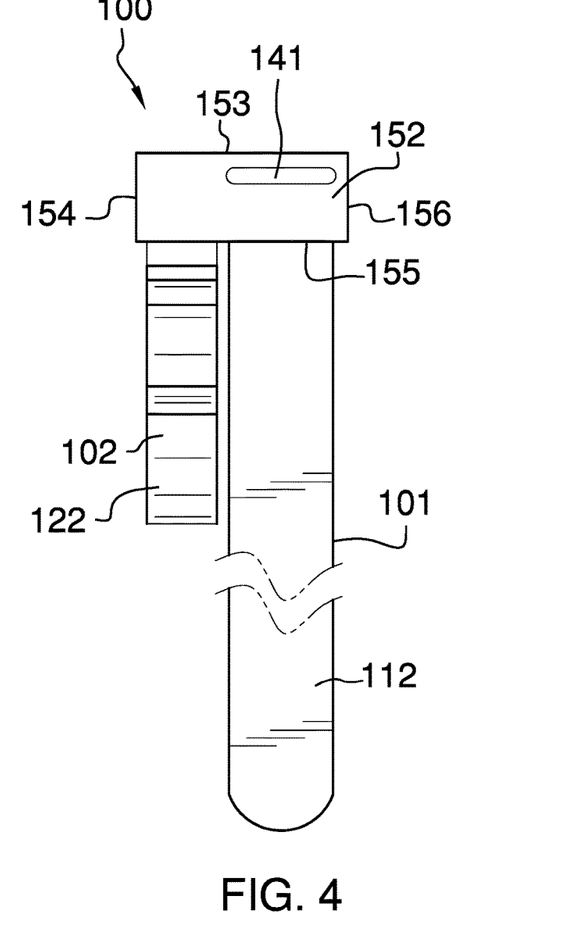
FIG. 4 is a front view of an embodiment of the disclosure.
Figure 5:
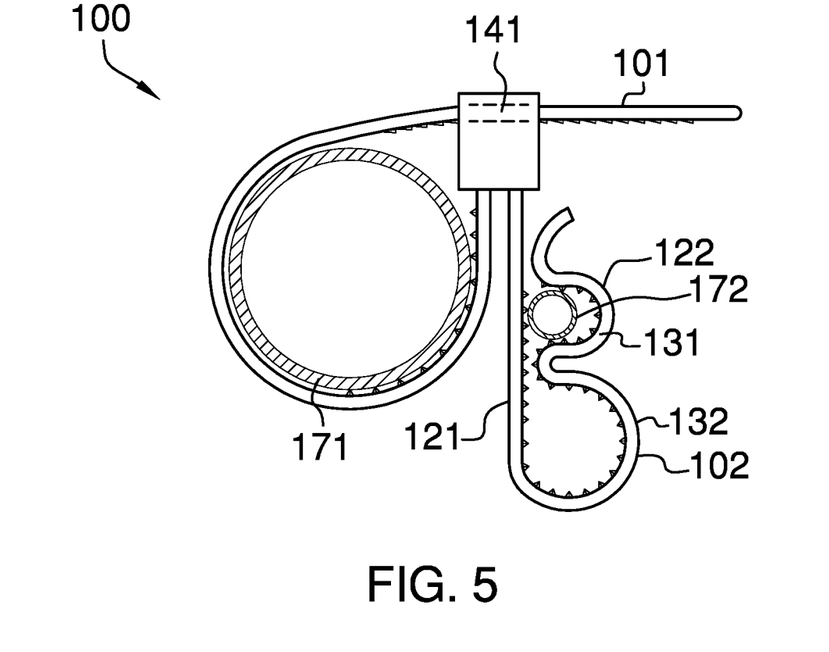
FIG. 5 is an in use view of an embodiment of the disclosure.
Figure 6:
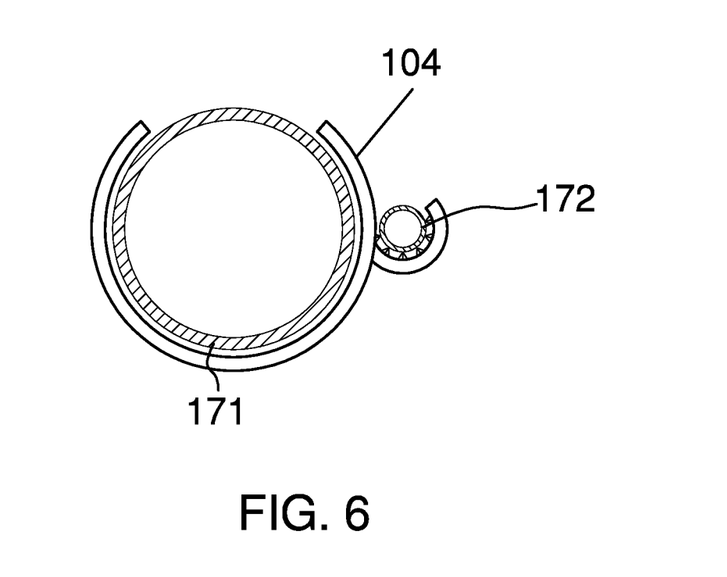
FIG. 6 is a detail view of an embodiment of the disclosure.
Figure 7:
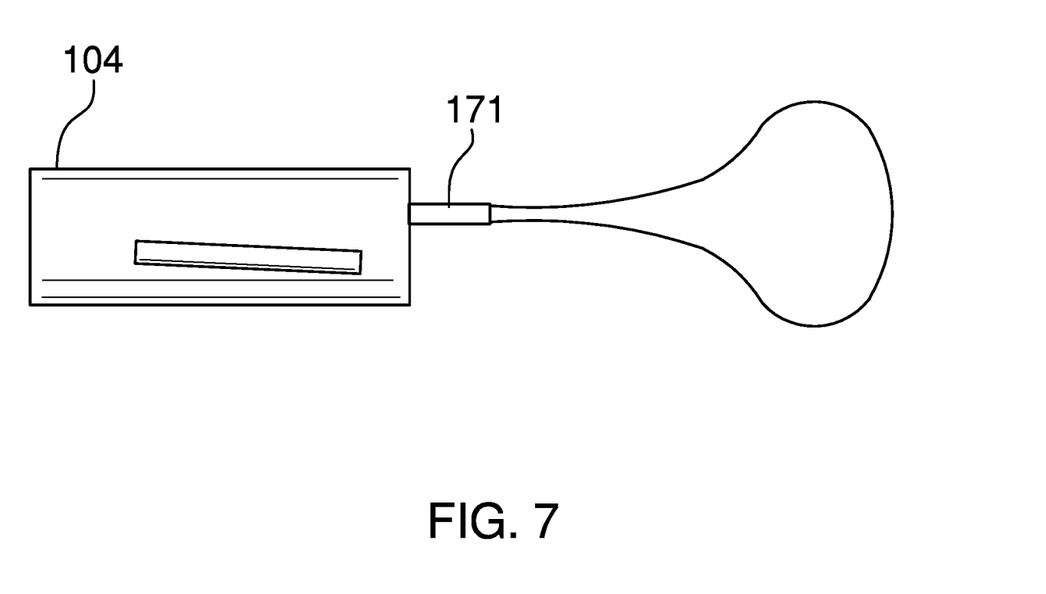
FIG. 7 is a side view of an embodiment of the disclosure.
Figure 8:
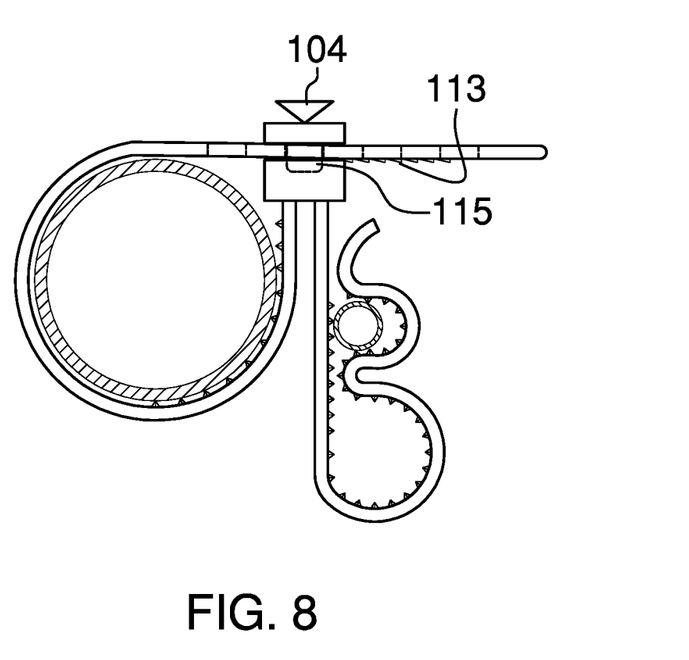
FIG. 8 is another view of an embodiment of the disclosure.

Detailed reference will now be made to one or more potential embodiments of the disclosure, which are illustrated in FIGS. 1 through 8.

The medical tube securing device 100 (hereinafter invention) is a fastener. The invention 100 is adapted for use with a first catheter 171. The invention 100 is further adapted for use with a second catheter 172. The invention 100 fastens the first catheter 171 to the second catheter 172. The invention 100 comprises an intubation strap 101, a gastric clip 102, and a latch 103. The intubation strap 101 and the gastric clip 102 are attached to the latch 103. The intubation strap 101 and the latch 103 attach the first catheter 171 to the invention 100. The gastric clip 102 attaches the second catheter 172 to the invention 100 thereby securing the first catheter 171 to the second catheter 172. In the first potential embodiment of the disclosure, the first catheter 171 is an endotracheal device 171 and the second catheter 172 is a gastric catheter 172. In a second potential embodiment of the disclosure, the invention 100 further comprises a bite guard 104 that prevents the patient from biting one or more devices selected from the group consisting of the endotracheal device 171 or the gastric catheter 172. The endotracheal device 171 refers to what is informally called a breathing tube. The gastric catheter 172 refers to what is informally called a feeding tube.

The intubation strap 101 is a sheeting material that is formed in the shape of a rectangular strip. The intubation strap 101 is wrapped around the endotracheal device 171 and is secured to the latch 103. The intubation strap 101 fastens the endotracheal device 171 to the invention 100. The intubation strap 101 attaches to the fifth face 155 of the latch 103. The intubation strap 101 comprises a first surface 111 and a second surface 112. The first surface 111 further comprises a plurality of knurls 113. The first surface 111 is the surface of the intubation strap 101 with the greatest surface area. The second surface 112 is the surface of the intubation strap 101 that is distal from the first surface 111.

Each of the plurality of knurls 113 is a hemispherical structure that is mounted on the first surface 111. Each of the plurality of knurls 113 is identical. Each of the plurality of knurls 113 is an elastic structure that deforms slightly when brought in contact with the endotracheal device 171. This deformation increase the surface area of contact between the first surface 111 and the endotracheal device 171 thereby improving the security of the grip of the invention 100. Each of the plurality of knurls 113 also deforms when the intubation strap 101 is inserted into the latch 103. This deformation of the plurality of knurls 113 creates a force as each of the plurality of knurls 113 attempts to return to its relaxed shape. The forces generated by each of the plurality of knurls 113 secures the intubation strap 101 within the latch 103.

The gastric clip 102 is a cantilever V spring. The gastric clip 102 fastens the gastric catheter 172 to the invention 100 and, by implication, the endotracheal device 171. The gastric clip 102 comprises a first cantilever structure 121 and a second cantilever structure 122. The first cantilever structure 121 is further defined with a first fixed end 123 and a first free end 125. The second cantilever structure 122 is further defined with a second fixed end 124 and a second free end 126. The second cantilever structure 122 comprises a first arch 131 and a second arch 132.

The first cantilever structure 121 is a straight shaft that forms a first arm of the cantilever V spring formed by the gastric clip 102. The second cantilever structure 122 is a curved linear structure that forms the second arm of the cantilever V spring formed by the gastric clip 102. The first fixed end 123 of the first cantilever structure 121 attaches to the second fixed end 124 of the second cantilever structure 122. The first free end 125 of the first cantilever structure 121 attaches to the fifth face 155 of the latch 103. The space between the second free end 126 and the first cantilever structure 121 forms the mouth of the gastric clip 102 into which the gastric catheter 172 is inserted.

The first arch 131 is an arc that is formed in the shape of a segment of the circumference of a circle that is defined by a first radius. The first radius is selected such that the first arch 131 will enclose the gastric catheter 172 holding it against the first cantilever structure 121. The second arch 132 is an arc that is formed in the shape of a segment of the circumference of a circle that is defined by a second radius. The second radius is selected such that the second arch 132 will enclose the gastric catheter 172 holding it against the first cantilever structure 121. The span of the first radius of the first arch 131 and the span of the second radius of second arch 132 differ such that gastric catheter 172 of differing outer diameters may be used with the invention 100.

As the second cantilever structure 122 is moved away from the first cantilever structure 121 a resisting force is created that returns the second cantilever structure 122 to its relaxed shape. After the gastric catheter 172 is placed into the gastric clip 102, the return of the second cantilever structure 122 to its relaxed shape will secure the gastric catheter 172 to the gastric clip 102.

The latch 103 is a device to which the intubation strap 101 is fastened such that the intubation strap 101 is fixed in position after the endotracheal device 171 is secured. The latch 103 is a rectangular block structure. The latch 103 further comprises a strap channel 141. The strap channel 141 is offset such that the strap channel 141 does not pass through the center of the latch 103. The latch 103 is further defined with a first face 151, a second face 152, a third face 153, a fourth face 154, a fifth face 155, and a sixth face 156.

The first face 151 is the face of the latch 103 through which the strap channel 141 is formed. The second face 152 is the face of the latch 103 that is distal from the first face 151. The strap channel 141 forms an opening in the second face 152. The third face 153 is the face of the latch 103 that is distal from the fifth face 155. The fourth face 154 is the face of the latch 103 that joins the first face 151, the second face 152, the third face 153, and the fifth face 155. The fifth face 155 is the face of the latch 103 that is distal from the strap channel 141. The sixth face 156 is the face of the latch 103 that is distal from the fourth face 154.

The strap channel 141 is a negative space that is formed within the latch 103. The strap channel 141 is formed in the shape of a rectangular block. The strap channel 141 forms a radial hole through the rectangular block structure of the latch 103 from the first face 151 through to the second face 152. The span of the strap channel 141 in the direction from the third face 153 to the fifth face 155 is less than the span of distance from the second surface 112 of the intubation strap 101 to the most distal point of any knurl selected from the plurality of knurls 113 thereby forcing each of the plurality of knurls 113 to be deformed as the intubation strap 101 is inserted into the strap channel 141.

In the first potential embodiment of the disclosure, each of the plurality of knurls 113 is formed in the shape of a triangular prism. The strap channel 141 is further formed with a pawl 115 such that when the first surface 111 is inserted into the strap channel 141, a ratchet similar to a cable tie is formed that secures the intubation strap within the strap channel 141.

In a second potential embodiment of the disclosure, the strap channel 141 is further formed with a quick release 114 that will release the intubation strap 101 from the strap channel 141. Methods to form ratchets for cable ties and to release ratchets are well known in the mechanical arts.

In a third potential embodiment of the disclosure, the invention 100 further comprises a bite guard 104. The bite guard 104 is a rigid structure that is formed in the shape of a horizontal segment of a cylinder.

The endotracheal device 171 and the gastric catheter 172 are placed within the lumen of the bite guard 104. The bite guard 104 is placed in the mouth of the patient. The rigid structure of the bite guard 104 prevents the patient from collapsing the lumen of either the endotracheal device 171 or the gastric catheter 172 through an inadvertent bite.

The span of the inner diameter of the cylinder that forms the bite guard 104 is greater than the sum of the span of the outer diameter of the endotracheal device 171 and the span of the outer diameter of the gastric catheter 172 such that the endotracheal device 171 and the gastric catheter 172 can be placed in the lumen formed by the bite guard 104.

The following definitions were used in this disclosure:

Adhesive: As used in this disclosure, an adhesive is a chemical substance that can be used to adhere two or more objects to each other. Types of adhesives include, but are not limited to, epoxies, polyurethanes, polyimides, or cyanoacrylates, silicone, or latex based adhesives.

Arc: As used in this disclosure, an arc refers to a portion of a circumference or a curved perimeter. When applied to an angle, the arc also refers to a measure of an angular span as measured from a circle at the vertex formed by the sides of the angle.

Arch: As used in this disclosure, an arch refers to a curved edge or surface that bounds a definable negative space.

Cable Tie: As used in this disclosure, a cable tie is a type of fastener that is used to tie two objects together. The cable tie has a box end and an open end. The box end further comprises a gear like structure wherein when the open end is inserted into the gear like structure, the gear like structure acts as a ratchet that prevents the open end from being removed from the gear like structure.

Cantilever: As used in this disclosure, a cantilever is a beam or other structure that projects away from an object and is supported on only one end. A cantilever is further defined with a fixed end and a free end. The fixed end is the end of the cantilever that is attached to the object. The free end is the end of the cantilever that is distal from the fixed end.

Cantilever V Spring: As used in this disclosure, a cantilever V spring is a torsion spring that is formed in a chevron shape. The cantilever V spring comprises a first cantilever structure and a second cantilever structure wherein the fixed end of the first cantilever structure is attached to the fixed end of the second cantilever structure. Within this structure, when a force is applied to the cantilever V spring such that the first cantilever structure moves relative to from the second cantilever structure the force deforms the cantilever V spring in an elastic manner that: 1) resists the application of the force; and 2) stores the energy deformation such that when the force is no longer applied the cantilever V spring returns to its relaxed shape. Depending on the application, a cantilever V spring can be considered a torsion spring, a tension spring, or a compression spring.

Catheter: As used in this disclosure, a catheter is a flexible tube that is inserted into the body through which fluids may be introduced into or removed from the body.

Chevron: As used in this disclosure, chevron is a term that is used to describe an object that has the shape of a U or a V.

Cylinder: As used in this disclosure, a cylinder is a geometric structure defined by two identical flat and parallel ends, also commonly referred to as bases, which are circular in shape and connected with a single curved surface, referred to in this disclosure as the face. The cross section of the cylinder remains the same from one end to another. The axis of the cylinder is formed by the straight line that connects the center of each of the two identical flat and parallel ends of the cylinder. Unless otherwise stated within this disclosure, the term cylinder specifically means a right cylinder which is defined as a cylinder wherein the curved surface perpendicularly intersects with the two identical flat and parallel ends. Diameter: As used in this disclosure, a diameter of an object is a straight line segment that passes through the center of an object. The line segment of the diameter is terminated at the perimeter or boundary of the object through which the line segment of the diameter runs.

Elastic: As used in this disclosure, an elastic is a material or object that deforms when a force is applied to it and that is able to return to its relaxed shape after the force is removed. A material that exhibits these qualities is also referred to as an elastomeric material.

Endotracheal Device: As used in this disclosure; an endotracheal device is a medical device. The endotracheal device is a catheter that is inserted through the oral or nasal cavity into the lungs of a patient for the purposes that include, but are not limited to: 1) aiding the patient with respiration; and 2) blocking the passage of gastrointestinal fluids through the trachea. The types of endotracheal devices considered within this disclosure include, but are not limited to, a preformed endotracheal device, a pediatric endotracheal device, a reinforced tube endotracheal device, a double lumen endotracheal device. Most, though not all, endotracheal devices further comprise a cuff. The cuff is an inflatable bladder that seals the trachea such that all gas flow through the trachea flows through the endotracheal device.

Fastener: As used in this disclosure, a fastener is a device that is used to join or affix two objects. Fasteners generally comprise a first element which is attached to the first object and a second element which is attached to the second object such that the first element and the second element are joined to affix the first object and the second object.

Gastric Catheter: As used in this disclosure, a gastric catheter refers to what is commonly called a feeding tube that is inserted into the esophagus for the purpose of providing nutrition to a patient.

Horizontal Segment: As used in this disclosure, a horizontal segment refers to a structure that is formed from a prism or cylinder that is truncated by a single plane that is parallel to the center axis of the prism or cylinder.

Knurl: As used in this disclosure, a knurl refers to a small knob that projects from a surface. The knob is often, but not necessarily semi-spherical in shape. An object is referred to as "knurled" when the exterior surface of the object is comprises a plurality of knurls arranged in a regular pattern.

Latch: As used in this disclosure, a latch is a fastening or locking mechanism. The use of the term latch does not necessarily but often implies the insertion of an object into a notch or cavity.

Lumen: As used in this disclosure, a lumen refers to the hollow channel within a hose, tube, or pipe through which fluid is transported.

Negative Space: As used in this disclosure, negative space is a method of defining an object through the use of open or empty space as the definition of the object itself, or, through the use of open or empty space to describe the boundaries of an object.

Patient: As used in this disclosure, a patient is a person who is designated to receive a medical treatment, therapy or service. The term patient may be extended to an animal when used within the context of the animal receiving veterinary treatment or services Perimeter: As used in this disclosure, a perimeter is one or more curved or straight lines that bounds an enclosed area on a plane or surface. The perimeter of a circle is commonly referred to as a circumference.

Prism: As used in this disclosure, a prism is a 3 dimensional geometric structure wherein: 1) the form factor of two faces of the prism correspond to each other; and, 2) the two corresponding faces are parallel to each other. In this disclosure, when further description is required a prism will be named for the geometric or descriptive name of the form factor of the two corresponding faces. If the form factor of the two corresponding faces has no clearly established or well-known geometric or descriptive name, the term irregular prism will be used. The center axis of a prism is defined as a line that joins the center point of the first corresponding face of the prism to the center point of the second corresponding face of the prism. The center axis of a prism is otherwise analogous the center axis of a cylinder.

Radial hole: As used in this disclosure, a radial hole comprises a hole that is formed through a solid cylinder such that: 1) the formed hole is cylindrical; 2) the center axis of the formed hole is perpendicular to the center axis of the solid cylinder; and, 3) the center axis of the formed hole intersects the center axis of the solid cylinder. When the term radial hole is applied to a pipe, or other hollow cylindrical object, the term applies to two holes that are formed in the surface of the pipe in a manner that is consistent with the solid cylinder definition. When the term radial hole is applied to a prism formed from an N-gon when N is an even number, the assumption should be made that the center axis is formed by a line that connects the center of the first corresponding face of the prism to the center of the second corresponding face of the prism.

Radius: As used in this disclosure, a radius refers to a line segment that: 1) connects the center of a circle to the circumference of the circle; or, 2) connects the center of a sphere to the surface of the sphere. The span of the radius of a circle or sphere will be one half of the span of the diameter of the circle or sphere.

Ratchet: As used in this disclosure, a ratchet is a device comprising a pawl or hinged catch that engages the sloping teeth of a wheel or bar permitting motion in one direction only.

Rectangular Block: As used in this disclosure, a rectangular block refers to a three dimensional structure comprising six rectangular surfaces formed at right angles. Within this disclosure, a rectangular block may further comprises rounded edges and corners.

Sheeting: As used in this disclosure, sheeting is a material, such as a textile, a plastic, or a metal foil, in the form of a thin flexible layer or layers.

Spring: As used in this disclosure, a spring is a device that is used to store mechanical energy. This mechanical energy will often be stored by: 1) deforming an elastomeric material that is used to make the device; 2) the application of a torque to a rigid structure; or 3) a combination of the previous two items.

Strap: As used in this disclosure a strap is a strip of leather, cloth, or other flexible material that is used to fasten, secure, carry, or hold onto something.

Strip: As used in this disclosure, the term describes a long thin object of uniform width. Strips are often rectangular blocks in shape.

Tape: As used in this disclosure, tape refers to a flexible and narrow strip of textile or sheeting that fastens, secures, or strengthens an object.

Torsion Spring: As used in this disclosure, a torsion spring is a mechanical device that stores mechanical energy through an opposing torque when the mechanical device is twisted. The torsion spring will return to its original relaxed shape when the twisting force is removed.

Truncated: As used in this disclosure, a geometric object is truncated when an apex, vertex, or end is cut off by a line or plane.

Tube: As used in this disclosure, a tube is a hollow cylindrical device that is used for transporting liquids and gases. The line that connects the center of the first base of the cylinder to the center of the second base of the cylinder is referred to as the center axis of the tube or the centerline of the tube. In this disclosure, the terms inner diameter of a tube and outer diameter of a tube are used as they would be used by those skilled in the plumbing arts.

Vertical Segment: As used in this disclosure, a vertical segment refers to a structure that is formed from a prism or cylinder that is truncated by one or more planes that intersect the center axis of the prism or cylinder.

With respect to the above description, it is to be realized that the optimum dimensional relationship for the various components of the invention described above and in FIGS. 1 through 8 include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

What is claimed is:

1. A fastening device comprising:
an intubation strap, a gastric clip, and a latch;
wherein the intubation strap and the gastric clip are attached to the latch;
wherein the fastening device is adapted for use with a first catheter;
wherein the fastening device is further adapted for use with a second catheter;
wherein the fastening device fastens the first catheter to the second catheter;
wherein the intubation strap and the latch attach the first catheter to the fastening device;
wherein the gastric clip attaches the second catheter to the fastening device thereby securing the first catheter to the second catheter;
wherein the intubation strap is a sheeting material;
wherein the intubation strap is formed in the shape of a rectangular strip;
wherein the intubation strap is wrapped around the first catheter;
wherein the intubation strap is secured to the latch;
wherein the intubation strap comprises a first surface, a second surface, and a plurality of knurls;

wherein the plurality of knurls are attached to the first surface;
wherein the second surface is distal from the first surface;
wherein each of the plurality of knurls is a hemispherical structure;
wherein each of the plurality of knurls is identical;
wherein each of the plurality of knurls is an elastic structure;
wherein the plurality of knurls secure the first catheter within the intubation strap;
wherein the gastric clip fastens the second catheter to the fastening device;
wherein the latch is a rectangular block structure;
wherein the latch further comprises a strap channel;
wherein the strap channel is a negative space that is formed within the latch;
wherein the strap channel is formed in the shape of a rectangular block;
wherein the intubation strap is inserted into the strap channel;
wherein the latch is further defined with a first face, a second face, a third face, a fourth face, a fifth face, and a sixth face;
wherein the fastening device further comprises a bite guard;
wherein the bite guard is a rigid structure that is formed in the shape of a horizontal segment of a cylinder;
wherein the span of the lumen of the cylinder that forms the bite guard is greater than the sum of the span of the outer diameter of the first catheter and the span of the outer diameter of the second catheter such that the first catheter and the second catheter can be placed in the lumen formed by the bite guard;
wherein the first catheter and the second catheter are placed within the lumen of the bite guard;
wherein the bite guard protects one or more devices selected from the group consisting of the first catheter and the second catheter;
wherein the bite guard is placed in the mouth of the patient.

2. The fastening device according to claim 1
wherein the gastric clip comprises a first cantilever structure and a second cantilever structure;
wherein the first cantilever structure is further defined with a first fixed end and a first free end;
wherein the second cantilever structure is further defined with a second fixed end and a second free end;
wherein the first fixed end of the first cantilever structure attaches to the second fixed end of the second cantilever structure;
wherein the first free end of the first cantilever structure attaches to the latch.

3. The fastening device according to claim 2
wherein the first cantilever structure is a straight shaft;
wherein the second cantilever structure is a curved linear structure.

4. The fastening device according to claim 3
wherein the second cantilever structure comprises a first arch and a second arch;
wherein the first arch is an arc that is formed in the shape of a segment of the circumference of a circle that is defined by a first radius;
wherein the second arch is an arc that is formed in the shape of a segment of the circumference of a circle that is defined by a second radius;
wherein an arch selected from the first arch and the second arch encloses the second catheter holding it against the first cantilever structure.

5. The fastening device according to claim 4 wherein a span of the first radius of the first arch and span of the second radius of second arch are different from each other.

6. The fastening device according to claim 5
wherein the second gastric catheter is inserted into a space between the second free end and the first cantilever structure;
wherein as the second cantilever structure is moved away from the first cantilever structure, a resisting force is created that returns the second cantilever structure to its relaxed shape.

7. The fastening device according to claim 6 wherein the latch is a device to which the intubation strap is fastened such that the intubation strap is fixed in position after the first catheter is secured.

8. The fastening device according to claim 7 wherein the strap channel forms a radial hole through the rectangular block structure of the latch from the first face through to the second face.

9. The fastening device according to claim 8 wherein the strap channel is offset such that the strap channel does not pass through the center of the latch.

10. The fastening device according to claim 9 wherein the span of the strap channel in the direction from the third face to the fifth face is less than the span of distance from the second surface of the intubation strap to the most distal point of any knurl selected from the plurality of knurls thereby forcing each of the plurality of knurls to be deformed as the intubation strap is inserted into the strap channel.

11. The fastening device according to claim 10 wherein the intubation strap is attached to the fifth face of the latch.

12. The fastening device according to claim 11 wherein the first free end of the first cantilever structure attaches to the fifth face of the latch.

13. The fastening device according to claim 12
wherein the first catheter is an endotracheal device;
wherein the second catheter is a gastric catheter.

\* \* \* \* \*